United States Patent
Hartl

(10) Patent No.: US 8,850,869 B2
(45) Date of Patent: Oct. 7, 2014

(54) SENSOR ELEMENT

(75) Inventor: Helmut Hartl, Vienna (AT)

(73) Assignee: BC Tech Holding AG, Chur (CH)

( * ) Notice: Subject to any disclaimer, the term of this patent is extended or adjusted under 35 U.S.C. 154(b) by 1581 days.

(21) Appl. No.: 11/905,760

(22) Filed: Oct. 3, 2007

(65) Prior Publication Data

US 2009/0008250 A1    Jan. 8, 2009

(30) Foreign Application Priority Data

Jul. 5, 2007  (DE) .......................... 10 2007 031 451
Jul. 13, 2007 (DE) .......................... 10 2007 033 105

(51) Int. Cl.
*G01N 27/07* (2006.01)
*G01N 33/28* (2006.01)

(52) U.S. Cl.
CPC ............ *G01N 27/07* (2013.01); *G01N 33/2835* (2013.01)
USPC ..... 73/31.05; 73/23.2; 422/82.01; 422/82.02; 422/83; 422/98

(58) Field of Classification Search
USPC ................ 29/432.2, 428, 458, 469, 705, 801, 29/283.5, 593, 507, 592.1; 204/409
See application file for complete search history.

(56) References Cited

U.S. PATENT DOCUMENTS

| | | | | |
|---|---|---|---|---|
| 3,816,811 A | * | 6/1974 | Cmelik K | 324/667 |
| 4,905,655 A | * | 3/1990 | Maekawa | 123/494 |
| 4,939,468 A | * | 7/1990 | Takeuchi | 324/690 |
| 5,089,783 A | * | 2/1992 | Kapsokavathis et al. | 324/672 |
| 5,124,655 A | * | 6/1992 | Takeuchi et al. | 324/690 |
| 7,191,505 B2 | | 3/2007 | Hartl et al. | |
| 2005/0121323 A1 | * | 6/2005 | Hartl et al. | 204/409 |

FOREIGN PATENT DOCUMENTS

| | | |
|---|---|---|
| DE | 9317351 | 1/1994 |
| DE | 10242301 | 3/2004 |
| DE | 69433691 | 4/2005 |

* cited by examiner

*Primary Examiner* — Paul Hyun
*Assistant Examiner* — Robert Eom
(74) *Attorney, Agent, or Firm* — Welsh Flaxman & Gitler LLC

(57) ABSTRACT

A sensor element for a sensor or measuring device for measuring fluids, with a housing, the interior of which is sealed toward the outside and through which the fluid to measured can flow, and with at least one electrode arrangement in the housing interior, the electrode arrangement having at least one electrode and forming at least one measuring path.

7 Claims, 2 Drawing Sheets

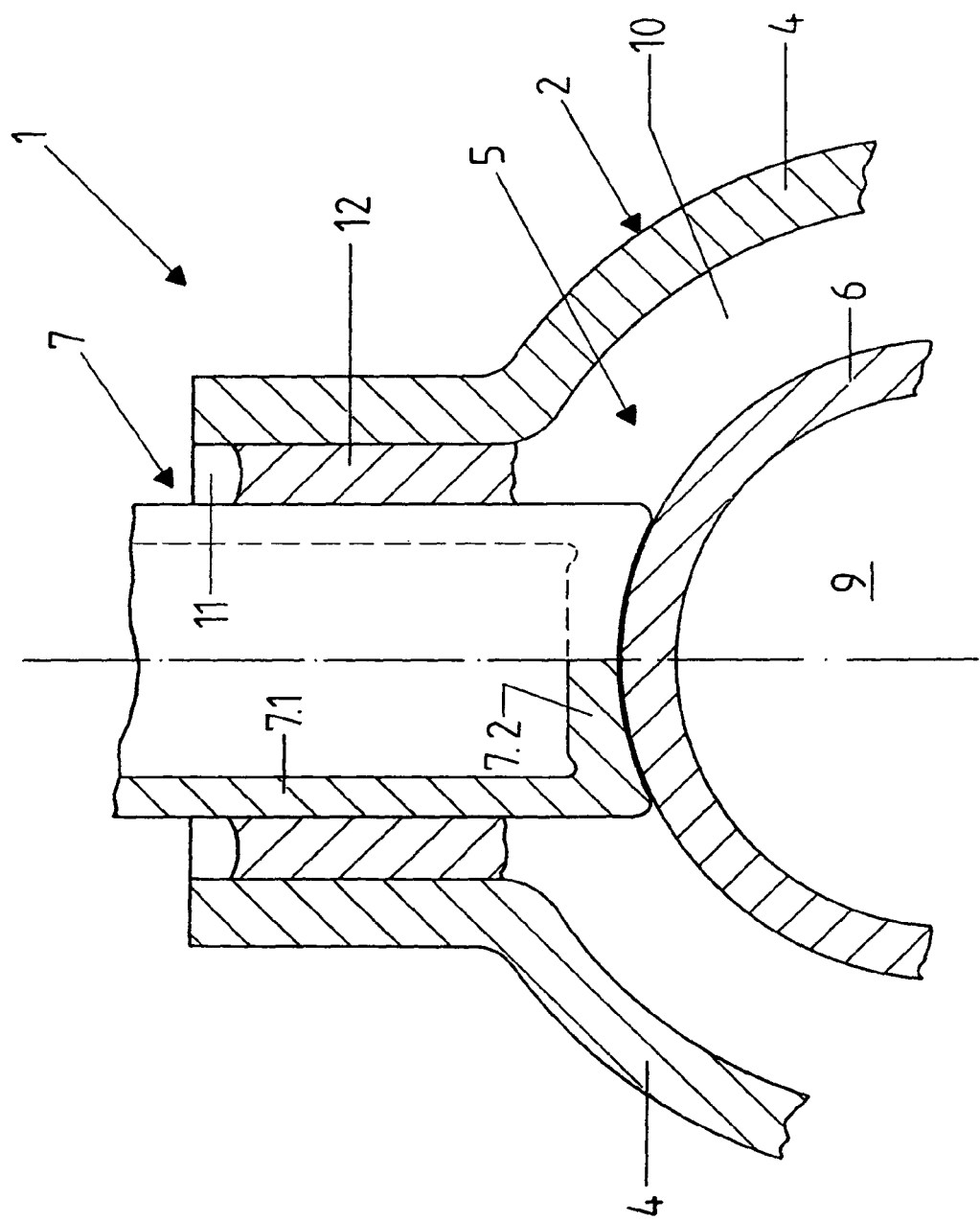

SENSOR ELEMENT

BACKGROUND OF THE INVENTION

The invention relates to a sensor element for measuring impurities or additives in fluids, or determining the concentration of impurities or additives in fluids.

Sensor elements for a sensor or for measuring devices for measuring impurities or additives in fluids, in particular also for determining the concentration of such impurities or additives in fluids or liquids, for example in liquid fuels or propellants, e.g. oil, gasoline, diesel fuel, etc. are known in the art (U.S. Pat. No. 7,191,505 B2). Such sensor elements generally consist of a housing with an outwardly closed and sealed housing interior with at least one inlet and at least one outlet for the fluid which is to be measured and which flows through the housing interior and further consist of at least one electrode made of an electrically conductive material located in the housing interior. Between the electrode and an electrically conductive inner surface of the housing in the form of a counter-electrode a measuring path is formed for an electrical measurement, for example a resistance measurement and/or a capacitance measurement of the fluid flowing through the measuring path. The electrode, which is for example cup-shaped, then leads with its open end out of the housing interior through an electrically insulated bushing, so that a measuring device or measuring circuitry can be connected to said electrode. It is also known in the art that the housing of the sensor element is tube-shaped on partial lengths.

The disadvantage of known sensor elements is, for example, that their housings are manufactured through complex machining processes and/or that they consist of a plurality of individual parts, which have to be connected with each other tightly to form the sealed housing, thus resulting in increased manufacturing expense, for example.

It is an object of the invention to present a sensor element which eliminates the above disadvantages.

SUMMARY OF THE INVENTION

A sensor element for measuring impurities or additives is provided with a housing with a housing interior. The interior is sealed toward the outside of the housing and through which the fluid to be measured can flow. At least one housing inlet and at least one housing outlet for the fluid to be measured is provided along with at least one electrode arrangement located in the housing interior. The at least one electrode arrangement has at least one electrode and at least one measuring path between the at least one electrode and a counter-electrode, wherein the housing, between the at least one housing inlet and the at least one housing outlet includes a housing section with the electrode arrangement which is manufactured as one piece from a tube shaped metal raw material by means of cold forming.

BRIEF DESCRIPTION OF THE DRAWINGS

The invention is described in more detail below based on an exemplary embodiment with reference to the drawings, wherein:

FIG. 2 shows an enlarged partial view of a section corresponding to line l-l of FIG. 1.

DETAILED DESCRIPTION OF THE INVENTION

Figure 1:
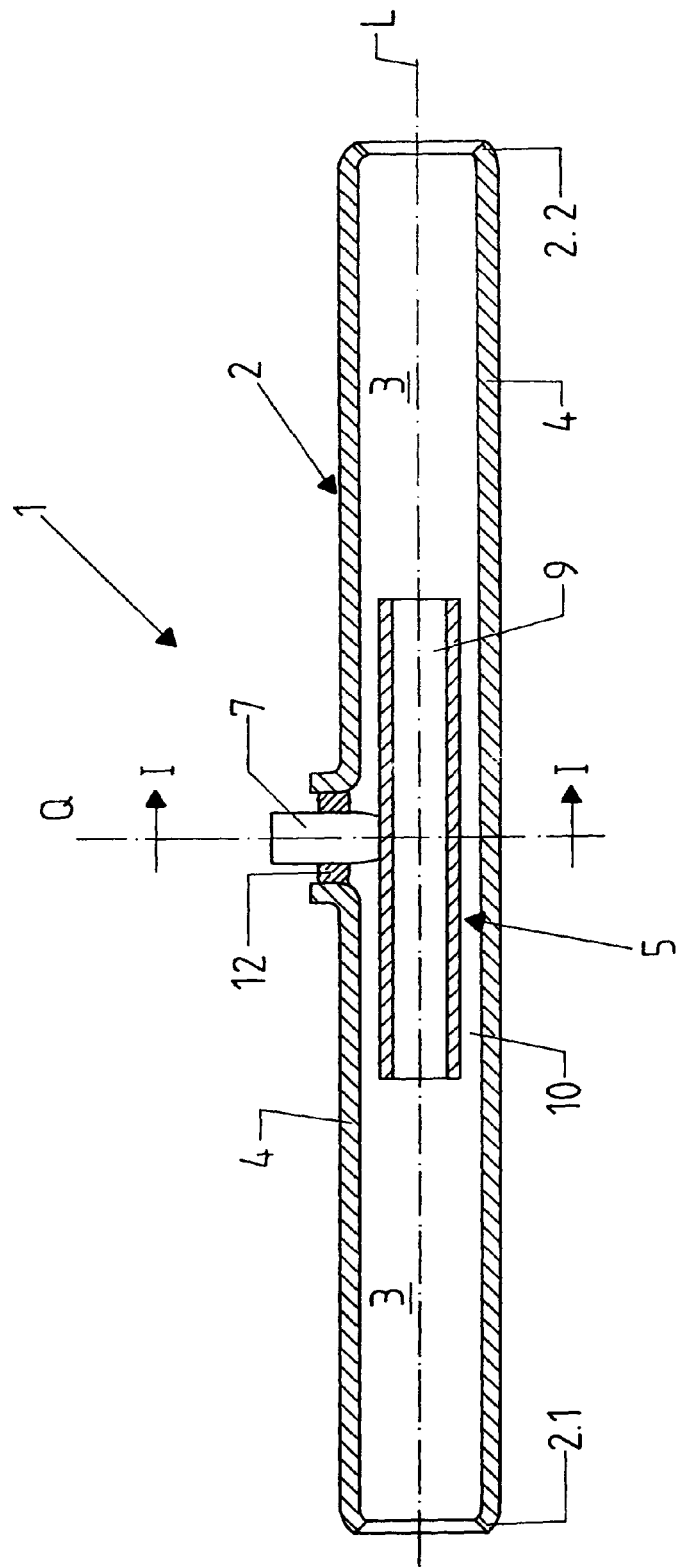
FIG. 1 shows a simplified view in longitudinal section of a sensor element according to the invention.

The sensor element generally designated 1 in FIGS. 1 and 2 is a component of a sensor or measuring device for measuring impurities and/or additives in fluids or liquids, in particular for determining the concentration of such impurities and/or or additives in fluids or liquids, for example in liquid fuels or propellants, such as oil, gasoline, diesel fuel, methanol (bio gas or bio diesel) by measuring electrical values, such as conductivity, capacitance, etc.

The sensor element 1 is made up of a housing 2, which in the depicted embodiment is an elongated tube-shaped housing, the housing interior 3 of which is open on the two ends 2.1 and 2.2 of the housing 2 for supplying (Arrow A) or removing (Arrow B) the fluid to be measured. Otherwise the housing interior 3 through which the measured fluid flows is tightly sealed.

The housing 2 is manufactured over its entire length as one piece from a tube-shaped metal and corrosion-resistant raw or tube material, for example of stainless steel, by cold forming or cold forging, namely with an essentially cylindrical inner and outer cross section and with a slightly reduced opening cross section at the ends 2.1 and 2.2. To increase the stability, the housing 2 can be manufactured with ribs or beads, in particular with ring-shaped ribs or beads, in the area of its ends, likewise produced from the housing wall 4 by cold forming.

In the middle of the sensor element 1, in the housing interior 3, an inner electrode arrangement 5 is provided, which consists of an electrode tube 6 arranged on the same axis as the longitudinal axis L of the housing 2 and open at both ends, and of an electrode holder 7, which is oriented with its axis radially to the longitudinal axis L of the housing 2 and which is held on the housing wall 4 at a bushing 8 with a liquid-tight and gas-tight seal and is also electrically insulated and leads out of the housing interior. The electrode tube 6 is fastened in its middle to the electrode holder 7. The electrode tube 6 and the electrode holder 7 are likewise made of a corrosion-resistant, metal material, for example stainless steel. The axial length of the electrode tube 6 is smaller than the total length of the housing 2 and makes up approximately one third the total length of the housing 2 in the depicted embodiment. Furthermore, the cylindrical outer diameter of the electrode tube 6 is smaller than the inner diameter of the tube-shaped housing 2, thus producing essentially two flow channels with a defined cross section in the area of the electrode arrangement 5 for the fluid flowing through the sensor element 1, namely an internal flow channel 9 within the electrode tube 6 that is open at both ends and an external ring-shaped flow channel 10 between the outer surface of the electrode tube 6 and the inner surface of the housing 2.

The electrode holder 7 is manufactured corresponding to FIG. 2 with a cup-shaped form with a cylindrical peripheral wall 7.1 and a bottom 7.2 and is connected at the bottom 7.2 with the electrode tube 6 in a suitable manner, for example by welding, e.g. laser or resistance welding, brazing, etc.

The bushing 8 consists of an opening 11 provided in the housing wall with a reinforced opening edge and of an insulating element 12 made of an electrically insulating material closing said opening. The inserted electrode holder 7 is sealed through the insulating element 12, so that it hermetically seals the housing interior 3 in the area of the bushing 8 to make it liquid-tight and/or gas-tight. The insulating element 12 is made of a suitable material for such bushings, e.g. glass, borosilicate glass, ceramic, ceramic material containing glass, plastic, for example epoxy resin, etc. The reinforced opening edge is formed for example from the material of the housing wall 4 as one piece with the housing 2 or from a ring that is tightly connected with the housing wall 4.

In application or use, the ring-shaped flow channel 10 is the actual measuring path, namely between the electrode formed by the electrode tube 6 and a counter-electrode formed by the housing wall 4 of the electrically conductive housing 2. The sensor element 1 in the depicted embodiment is mirror-symmetrical to a lateral plane QE arranged perpendicular to the longitudinal axis L and enclosing the axis of the electrode holder 7.

The electrode tube 6 arranged in the tube-shaped housing 2 produces, in a compact design of the sensor element 1, a relatively long measuring path formed by the flow channel 10, in particular also a measuring path resulting in an even flow of the fluid to be measured, which enables a measuring device with the sensor element 1 that is both highly sensitive and highly accurate. The use of the electrode tube 6 furthermore also achieves that only a part of the total volume of the fluid to be measured, defined especially by the aspect ratio of the flow channels 9 and 10, flows through the measuring path formed by the flow channel 10, so that said measuring path can be designed to be correspondingly long and with a reduced diameter for high measuring accuracy, while the overall flow resistance of the sensor element is kept small.

The sensor element 1 is characterized by high sensor or measuring sensitivity and high measuring accuracy by an especially simple design and therefore presents an optimized solution with respect to material and production costs, which makes it especially suitable for mass production. The housing 2 is manufactured entirely, i.e. over its entire length between the ends 2.1 and 2.2, including the housing section comprising the electrode arrangement 5, as one piece from the tube-shaped metal raw material, by means of cold forming.

The invention was described above based on an exemplary embodiment. It goes without saying that numerous modifications and variations are possible, without abandoning the underlying inventive idea upon which the invention is based.

For example, it was assumed above that the housing 2 is straight or essentially straight between its two ends 2.1 and 2.2. However, embodiments are also generally conceivable in which the housing, likewise manufactured as one piece from a tube-shaped raw material, is curved at least on a partial length, for example in the manner that the ends forming the inlet and outlet of the then for example U-shaped curved housing are located on a common side. With the use of at least one electrode as an electrode tube, the latter is then provided for example in a straight partial section of the housing.

REFERENCE LIST 1 sensor element
2 tube-shaped housing
2.1, 2.2 housing end
3 housing interior
4 housing wall
5 electrode arrangement
6 electrode tube
7 electrode holder
7.1 circumference of the cup-shaped electrode holder 7
7.2 bottom of the cup-shaped electrode holder
8 housing bushing for electrode holder 7
9, 10 flow channel
11 housing opening
12 insulating element
Arrow A, B direction of flow of the fluid to be measured
L longitudinal axis of housing 2
QE lateral plane

What is claimed is:

1. A sensor element for measuring impurities or additives in fluids or for determining a concentration of such impurities or additives in the fluids, the sensor element comprising a first tube-shaped electrically conductive housing with a housing interior which is sealed toward an outside of the tube-shaped electrically conductive housing and through which a fluid to be measured can flow, the sensor element has a housing inlet and a housing outlet for the fluid to be measured, and further comprising a second tube shaped electrode arrangement in the housing interior and forming at least one measuring path between the second tube shaped electrode and a counter-electrode formed by a housing wall of the first tube-shaped electrically conductive housing,
   wherein the second tube shaped electrode is open at both ends and oriented with an axis parallel to a longitudinal axis (L) of the first tube-shaped electrically conductive housing,
   wherein the at least one measuring path is a ring-shaped flow channel between an outer surface of the second tube shaped electrode and an inner surface of the first tube-shaped electrically conductive housing,
   wherein the second tube shaped electrode is held in the housing interior with an electrode holder, which is fastened to the first tube-shaped electrically conductive housing or a housing wall of the first tube-shaped electrically conductive housing so that it is electrically insulated,
   wherein the first tube-shaped electrically conductive housing has an opening formed by a bushing,
   wherein the electrode holder leads out of the housing interior through the bushing,
   wherein the electrode holder extends through an insulating element which fixes the electrode holder in the opening and tightly seals the housing interior at the opening, and
   wherein the insulating element is made of an electrically insulating material that tightly seals the housing interior and wherein the electrode holder has a cup-shaped form with a cylindrical peripheral wall and a curved bottom wall, the curved bottom wall of the electrode holder is shaped to connect flush with an outer wall of the second tube shaped electrode.

2. The sensor element according to claim 1, wherein between the housing inlet and the housing outlet of the first tube-shaped electrically conductive housing, a housing section comprising the second tube shaped electrode arrangement is manufactured as one piece from a tube-shaped metal raw material by means of cold forming.

3. The sensor element according to claim 1, wherein the first tube-shaped electrically conductive housing is straight or essentially straight.

4. The sensor element according to claim 1, wherein the first tube-shaped electrically conductive housing is curved on at least a partial section.

5. The sensor element according to claim 1, wherein the first tube-shaped electrically conductive housing has a reduced cross section as compared with a cross section of the housing interior in the area of at least one end forming a housing opening.

6. The sensor element according to claim 1, wherein the housing interior between the housing inlet and the housing outlet has an essentially consistent cross section.

7. The sensor element according to claim 1, wherein the insulating element is made of glass, ceramic or plastic.

* * * * *